US009316713B2

(12) United States Patent
Iwadate et al.

(10) Patent No.: US 9,316,713 B2
(45) Date of Patent: Apr. 19, 2016

(54) MAGNETIC RESONANCE IMAGING APPARATUS AND RF PULSE FOR NAVIGATOR AND IMAGING SEQUENCE APPLYING METHOD

(75) Inventors: Yuji Iwadate, Tokyo (JP); Kenichi Kanda, Tokyo (JP); Aki Yamazaki, Tokyo (JP)

(73) Assignee: General Electric Company, Schenectady, NY (US)

( * ) Notice: Subject to any disclaimer, the term of this patent is extended or adjusted under 35 U.S.C. 154(b) by 965 days.

(21) Appl. No.: 12/429,033

(22) Filed: Apr. 23, 2009

(65) Prior Publication Data
US 2009/0270720 A1    Oct. 29, 2009

(30) Foreign Application Priority Data

Apr. 24, 2008 (JP) ................................ 2008-113952

(51) Int. Cl.
*A61B 5/055* (2006.01)
*G01R 33/48* (2006.01)
*G01R 33/567* (2006.01)
*G01R 33/54* (2006.01)

(52) U.S. Cl.
CPC ......... *G01R 33/5676* (2013.01); *G01R 33/543* (2013.01); *G01R 33/546* (2013.01); *A61B 5/055* (2013.01)

(58) Field of Classification Search
CPC .. G01R 33/5676; G01R 33/20; G01R 33/543; G01R 33/546; A61B 5/055
USPC ........... 324/307, 309, 318; 600/410, 413, 420
See application file for complete search history.

(56) References Cited

U.S. PATENT DOCUMENTS

| 4,583,044 | A | * | 4/1986 | Case et al. ................... 324/309 |
| 4,999,580 | A | * | 3/1991 | Meyer et al. ................. 324/309 |
| 5,000,182 | A | | 3/1991 | Hinks |
| 5,251,128 | A | | 10/1993 | Crawford |
| 5,287,276 | A | | 2/1994 | Crawford et al. |
| 5,382,902 | A | | 1/1995 | Taniguchi et al. |
| 5,420,510 | A | | 5/1995 | Fairbanks et al. |

(Continued)

FOREIGN PATENT DOCUMENTS

| JP | 2007-098026 | 4/2007 |
| JP | 2007-111188 | 5/2007 |

OTHER PUBLICATIONS

Nezafat et al, Partial Field-of-View Spiral Phase-Contrast Imaging Using Complex Difference Processing, Magn Reson Med. Sep. 2006 ; 56(3): 676-680.*

(Continued)

*Primary Examiner* — Amanda Lauritzen Moher
*Assistant Examiner* — Serkan Akar

(57) ABSTRACT

A magnetic resonance imaging apparatus includes a scan section for executing a navigator sequence which transmits an RF pulse to a subject to obtain each magnetic resonance signal as navigator data. Upon execution of the navigator sequence, the scan section excites both a navigator area having two regions from which intensities of different navigator data signals are obtained, the two regions containing a body-moved region of the subject, and a region different from the two regions simultaneously, and transmits the RF pulse in such a manner that the phase of navigator data obtained from the different region differs from the phase of at least one region of navigator data obtained from the two regions.

16 Claims, 11 Drawing Sheets

(56) References Cited

U.S. PATENT DOCUMENTS

| | | |
|---|---|---|
| 5,499,629 A | 3/1996 | Kerr et al. |
| 5,779,636 A | 7/1998 | Kanazawa |
| 5,786,692 A * | 7/1998 | Maier et al. ............... 324/307 |
| 6,073,041 A | 6/2000 | Hu et al. |
| 6,144,201 A | 11/2000 | Miyazaki |
| 6,201,393 B1 | 3/2001 | Bernstein et al. |
| 6,275,720 B1 | 8/2001 | Du et al. |
| 6,486,668 B1 | 11/2002 | Ma |
| 6,489,766 B1 | 12/2002 | Alsop |
| 6,535,754 B2 | 3/2003 | Fishbein et al. |
| 6,690,963 B2 | 2/2004 | Ben-Haim et al. |
| 6,771,997 B2 | 8/2004 | Schaffer |
| 6,885,193 B2 | 4/2005 | Foxall |
| 6,894,494 B2 | 5/2005 | Stergiopoulos et al. |
| 7,012,603 B2 | 3/2006 | Chen et al. |
| 7,174,200 B2 | 2/2007 | Salerno et al. |
| 7,332,911 B2 | 2/2008 | Iwadate et al. |
| 7,343,193 B2 * | 3/2008 | Block et al. ............... 600/410 |
| 7,432,710 B2 | 10/2008 | Takei et al. |
| 2004/0092809 A1 | 5/2004 | DeCharms |
| 2004/0147832 A1 | 7/2004 | Fishbein et al. |
| 2006/0164087 A1 * | 7/2006 | Smink ............... 324/309 |
| 2006/0224062 A1 | 10/2006 | Aggarwal et al. |
| 2007/0080690 A1 | 4/2007 | Takei et al. |
| 2007/0088212 A1 * | 4/2007 | Takei et al. ............... 600/413 |
| 2007/0255130 A1 | 11/2007 | Du |
| 2009/0259120 A1 | 10/2009 | Iwadate et al. |

OTHER PUBLICATIONS

Mulkern et al, "A paradoxical signal intensity increase in fatty livers using opposed-phase gradient echo imaging with fat-suppression pulses", Pediatr Radiol (2008) 38:1099-1104.*

Pauly, J. et al., A k-Space Analysis of Small-Tip-Angle-Excitation, J. Magn. Reson., 1989, pp. 43-56, 81 (1).

Non-Final Office Action for U.S. Appl. No. 11/538,878 mailed Jan. 9, 2008; 12 pages.

Non-Final Office Action for U.S. Appl. No. 12/420,974 mailed Jun. 24, 2011; 13 pages.

Final Office Action for U.S. Appl. No. 12/420,974 mailed Oct. 18, 2011; 9 pages.

Non-Final Office Action for U.S. Appl. No. 12/420,974 mailed May 4, 2012; 18 pages.

* cited by examiner

| DISTANCE BETWEEN MAIN LOBE AND SIDE LOBE | NUMBER OF TURNS |
|---|---|
| 6.28 cm | 2 |
| 12.5 cm | 4 |
| 18.8 cm | 6 |
| 25.1 cm | 8 |

MAGNETIC RESONANCE IMAGING APPARATUS AND RF PULSE FOR NAVIGATOR AND IMAGING SEQUENCE APPLYING METHOD

CROSS REFERENCE TO RELATED APPLICATIONS

This application claims the benefit of Japanese Patent Application No. 2008-113952 filed Apr. 24, 2008, which is hereby incorporated by reference in its entirety.

BACKGROUND OF THE INVENTION

The embodiments described herein relate to a magnetic resonance imaging (MRI) apparatus and an RF pulse applying method, and particularly to a magnetic resonance imaging apparatus which executes scans for transmitting RF pulses to a subject and collecting or acquiring magnetic resonance signals from the subject thereby to generate an image of the subject, and an RF pulse applying method using RF pulses applied when a scan is performed.

A magnetic resonance imaging apparatus executes scans for applying an electromagnetic wave to a subject lying within a static magnetic field space thereby to excite spins of proton in the subject by a nuclear magnetic resonance phenomenon and acquiring magnetic resonance signals generated by the excited spins. This is of an apparatus that generates a slice image with respect to a tomographic plane of the subject, based on the magnetic resonance signals obtained by the scans.

There is a case in which body-motion artifacts occur in the generated slice image where body motion occurs in the subject upon imaging the subject using the magnetic resonance imaging apparatus. When, for example, the heart or abdominal region of the subject is imaged or photographed, body motion artifacts occur due to body motion such as breathing exercises, cardiac motion or the like, thus degrading the quality of the image.

Thus, there have been proposed methods for solving the problem of the degradation in the image due to the body motion artifacts. One method thereof is that upon imaging or photography under normal respiration, for example, an excitation section of a subject is corrected in real time according to a change in the position of a diaphragm and each magnetic resonance signal is always measured from the same section, thereby preventing the degradation in the image due to the body motion artifacts. An imaging sequence is changed or imaging data is selected through the use of acquired navigator echoes, thereby preventing degradation in image quality due to body motion artifacts (refer to, for example, Japanese Unexamined Patent Publication No. 2007-111188 and Japanese Unexamined Patent Publication No. 2007-98026).

However, as a result that as shown in a coronal image of FIG. 13, an imaging area IA for executing an imaging scan to acquire imaging data has overlapped with a navigator area NA corresponding to the position of acquisition of navigator data, signal disturbance due to slice interference occurs in the acquired navigator data. As indicated by a broken-line area of FIG. 14, noise occurs in a signal intensity profile obtained by plotting the relationship between a signal intensity I of acquired navigator data and a position L of a navigator area. Here, the broken-line area shown in FIG. 14 indicates a signal intensity profile corresponding to a portion where the imaging area IA and the navigator area NA shown in FIG. 13 overlap. In doing so, it became difficult to obtain a stable analytic result by the conventional navigator data analyzing method shown above.

Thus, there has been considered a method for suppressing the occurrence of signal disturbance due to the interference of an imaging scan by using phase information of navigator data.

The occurrence of the signal disturbance due to the interference of the imaging scan can be suppressed by using the phase information of the navigator data. A problem however arises in that since variations are easy to occur in the phase at a region low in signal intensity as shown in FIG. 15, it is difficult to obtain the result of analysis of navigator data stably, thus causing degradation in image quality.

It is desirable that the problem described previously is solved.

BRIEF DESCRIPTION OF THE INVENTION

In one aspect, a magnetic resonance imaging apparatus has a scan section for executing a navigator sequence which transmits an RF pulse to a subject to obtain each magnetic resonance signal as navigator data. Upon execution of the navigator sequence, the scan section excites both a navigator area having two regions from which intensities of different navigator data signals are obtained, containing a body-moved region of the subject, and a region different from the two regions simultaneously, and transmits the RF pulse in such a manner that the phase of navigator data obtained from the different region differs from the phase of at least one region of navigator data obtained from the two regions.

Preferably, the scan section transmits the RF pulse in such a manner that the intensity of a navigator data signal obtained from the different region falls between the intensities of the navigator data signals obtained from the two regions.

Preferably, the scan section transmits the RF pulse to a lung and a liver set as the two regions and a subcutaneous fat set as the different region, respectively.

Preferably, the scan section transmits the RF pulse to a subcutaneous fat set as the different region, which is located in a plane orthogonal to the navigator area.

Preferably, the scan section executes the navigator sequence in such a manner that the phase of navigator data obtained from the subcutaneous fat differs from the phase of navigator data obtained from the liver.

Preferably, the scan section executes the navigator sequence in such a manner that the intensity of a navigator data signal obtained from the subcutaneous fat becomes lower than the intensity of a navigator data signal obtained from the liver.

Preferably, the scan section executes the navigator sequence in such a manner that a gradient magnetic field at the navigator excitation assumes a spiral trajectory on a k space.

Preferably, the scan section transmits RF pulses for exciting the two regions and the different region in cylindrical form respectively.

Preferably, the number of turns at the time that the gradient magnetic field at the navigator excitation assumes a spiral trajectory on a k space, is determined based on an interval between the navigator area and the different region.

Preferably, a gradient magnetic field is generated so as to assume a spiral trajectory outside as viewed from the center of the k space.

Preferably, a gradient magnetic field is generated so as to assume a spiral trajectory in the center of the k space as viewed from outside the k space.

Another aspect provides an RF pulse applying method which executes a navigator sequence for transmitting an RF pulse to a subject and thereby obtaining each magnetic resonance signal as navigator data, including the steps of upon execution of the navigator sequence, exciting both a navigator area having two regions from which intensities of different navigator data signals are obtained, containing a body-moved region of the subject, and a region different from the two regions simultaneously; and transmitting the RF pulse in such a manner that the phase of navigator data obtained from the different region differs from the phase of at least one region of navigator data obtained from the two regions.

Preferably, the RF pulse is transmitted in such a manner that the intensity of a navigator data signal obtained from the different region falls between the intensities of the navigator data signals obtained from the two regions.

Preferably, the RF pulse is transmitted to a lung and a liver set as the two regions and a subcutaneous fat set as the different region, respectively.

Preferably, the RF pulse is transmitted to a subcutaneous fat set as the different region, which is located in a plane orthogonal to the navigator area.

Preferably, the navigator sequence is executed in such a manner that the phase of navigator data obtained from the subcutaneous fat differs from the phase of navigator data obtained from the liver.

Preferably, the navigator sequence is executed in such a manner that the intensity of a navigator data signal obtained from the subcutaneous fat becomes lower than the intensity of a navigator data signal obtained from the liver.

Preferably, the navigator sequence is executed in such a manner that a gradient magnetic field at the said navigator excitation assumes a spiral trajectory in a k space.

Preferably, RF pulses for exciting the two regions and the different region in cylindrical form respectively are transmitted.

Preferably, the number of turns at the time that the gradient magnetic field at the navigator excitation assumes a spiral trajectory on a k space, is determined based on an interval between the navigator area and the different region.

Aspects of the invention provide a magnetic resonance imaging apparatus capable of enhancing image quality by obtaining a stable result of analysis of navigator data, and an RF pulse applying method capable of improving image quality.

Embodiments of the present invention will be apparent from the following description as illustrated in the accompanying drawings.

DETAILED DESCRIPTION OF THE INVENTION

One embodiment according to the invention will be explained below with reference to the accompanying drawings.

Apparatus Construction

Figure 1:
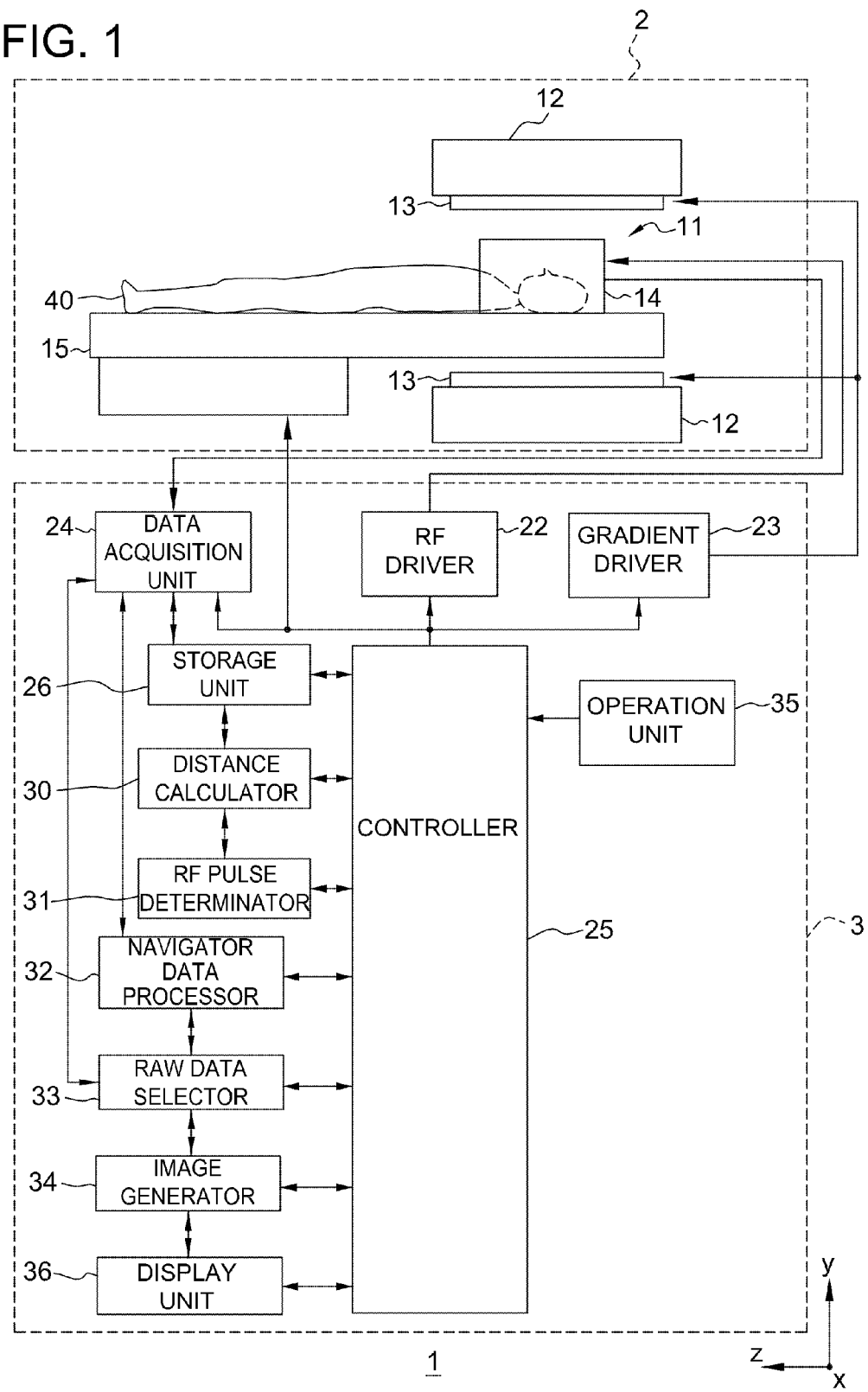
FIG. 1 is a constructional diagram showing a construction of an exemplary magnetic resonance imaging apparatus constructed by an RF coil unit.

FIG. 1 is a constructional diagram showing a construction of a magnetic resonance imaging apparatus configured by an RF coil unit employed in the one embodiment according to the invention. The present apparatus is one example illustrative of the embodiment of the invention.

As shown in FIG. 1, the magnetic resonance imaging apparatus 1 has a scan section 2 and an operation console section 3. Here, the scan section 2 has a static magnetic field magnet unit 12, a gradient coil unit 13, an RF coil unit 14 and a cradle 15. The operation console section 3 has an RF driver 22, a gradient driver 23, a data acquisition unit 24, a controller 25, a storage unit 26, a distance calculator 30, an RF pulse determiner 31, a navigator data processor 32, a raw data selector 33, an image generator 34, an operation unit 35 and a display unit 36.

The scan section 2 will be explained.

As shown in FIG. 1, the scan section 2 includes a static magnetic field space 11 in which an imaging slice area in a subject 40 is held or accommodated. The scan section 2 applies RF pulses to the corresponding imaging area of the subject 40 held in the static magnetic filed space 11 formed with a static magnetic field, based on a control signal outputted from the operation console unit 3 and executes a scan for acquiring each magnetic resonance signal from the imaging area thereof.

In the present embodiment, the scan section 2 repeatedly executes an imaging sequence IS for obtaining a magnetic resonance signal generated at an imaging area IA of the subject 40 as imaging data, and a navigator sequence NS for acquiring a magnetic resonance signal generated at a navigator area NA of the subject 40 as navigator data.

Respective constituent elements of the scan section 2 will be explained sequentially.

The static magnetic field magnet unit 12 is provided to form a static magnetic field in the static magnetic field space 11 with the subject 40 held therein. The static magnetic field magnet unit 12 is of a horizontal magnetic field type and forms a static magnetic field through a superconductive magnet (not shown) so as to extend along a body-axis direction (z direction) of the subject 40 placed in the static magnetic field space 11 with the subject 40 accommodated therein. Incidentally, the static magnetic field magnet unit 12 may be of a vertical magnetic field type in addition to the horizontal magnetic field type. Alternatively, the static magnetic field magnet unit 12 may be constituted of a permanent magnet.

The gradient coil unit 13 forms a gradient magnetic field in the static magnetic field space 11 to cause each magnetic resonance signal received by the RF coil unit 14 to have three-dimensional position information. The gradient coil unit 13 has gradient coils of three systems to form three types of gradient magnetic fields corresponding to a slice selection gradient magnetic field, a read gradient magnetic field and a phase encode gradient magnetic field.

The RF coil unit 14 is disposed so as to surround the subject 40, for example. The RF coil unit 14 transmits each RF pulse corresponding to an electromagnetic wave to the subject 40, based on a control signal supplied from the controller 25 within the static magnetic field space 11 formed with the static magnetic field by the static magnetic field magnet unit 12 thereby to form a high frequency magnetic field. Consequently, the spins of proton in the imaging slice area of the subject 40 are excited. The RF coil unit 14 receives an electromagnetic wave generated when each of the excited spins of proton in the imaging slice area of the subject 40 is returned to its original magnetization vector, as a magnetic resonance signal. The RF coil unit 14 may perform the transmission/reception of each RF pulse through the same RF coil.

In the present embodiment, the RF coil unit 14 transmits a navigator pulse in the navigator sequence NS and transmits an imaging pulse the imaging sequence IS.

Figure 2:
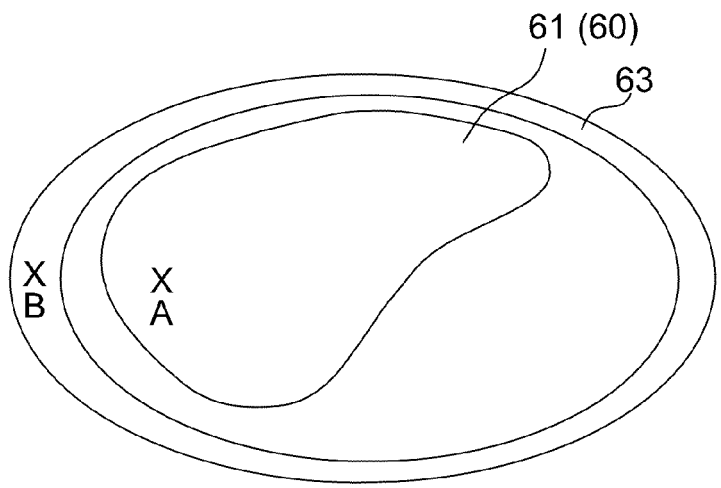
FIG. 2 is a diagram showing an axial transverse section of a subject.
Figure 3:
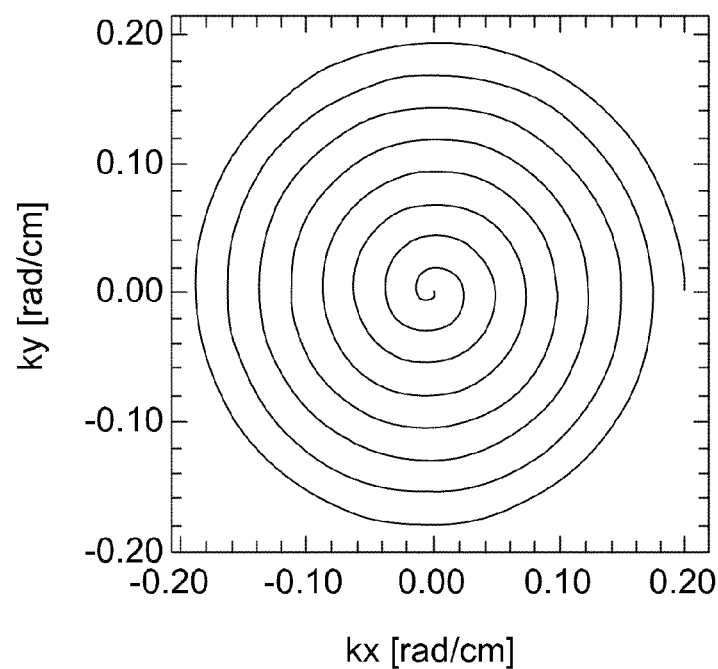
FIG. 3 is a diagram illustrating a k-space trajectory of a pencil beam that may be used with the magnetic resonance imaging apparatus shown in FIG. 1.
Figure 4:
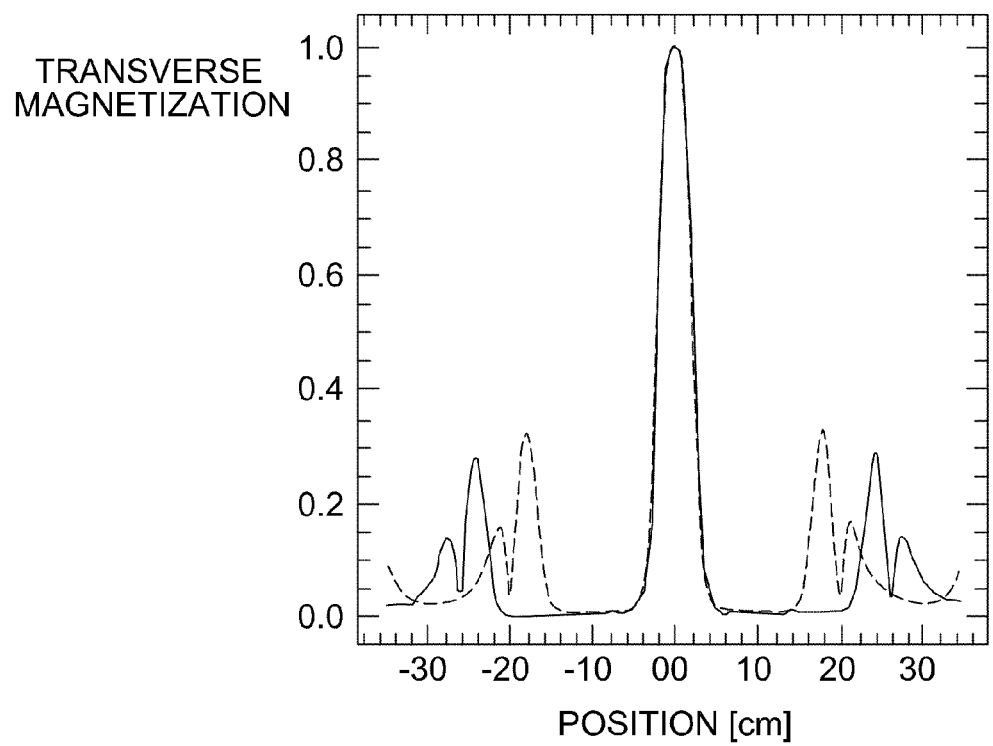
FIG. 4 is a diagram depicting transverse magnetization formed immediately after excitation of the pencil beam shown in FIG. 3.

FIG. 2 is a diagram showing an axial transverse section of the subject. X marks in the figure respectively indicate positions excited by RF pulses. FIG. 3 is a diagram illustrating a k-space trajectory formed upon excitation of a pencil beam. FIG. 4 is a diagram showing transverse magnetization formed immediately after the excitation of the pencil beam. A solid line indicates where the number of turns of a spiral trajectory at the excitation of the pencil beam is eight, whereas a dotted line indicates where the number of turns is six.

The navigator pulse is of an RF pulse for exciting a region body-moved in the navigator area and a region different from the region body-moved therein simultaneously.

In the present embodiment, as shown in FIG. 2, for example, the region body-moved in the navigator area is of a liver 61 or lung 60, and the region different from the body-moved region is of a subcutaneous fat 63. As shown in FIG. 2, the subcutaneous fat 63 corresponds to, for example, a subcutaneous fat 63 lying on the plane or surface that orthogonally intersects with the navigator area. As the navigator pulse, may be mentioned, for example, a pencil beam.

The pencil beam is of an exciting method used to excite only a cylindrical area. As shown in FIG. 3, the pencil beam produces or generates a gradient magnetic field in such a manner that it takes or assumes a spiral trajectory outside as viewed from the center of a k space or in the center thereof as viewed from outside. As to the transverse magnetization formed immediately after the above excitation by the pencil beam as shown in FIG. 4, a main lobe large in transverse magnetization is disposed in the center, and side lobes smaller in transverse magnetization than the main lobe are disposed on both sides.

In the present embodiment, the main lobe is located in the liver 61 and the lung 60, and each side lobe is located in the subcutaneous fat 63.

The cradle 15 has a table that places the subject 40 thereon. The cradle 15 moves the subject 40 placed on the table between the inside and outside of the static magnetic field space 11, based on a control signal supplied from the controller 25.

The operation console section 3 will be explained.

The operation console section 3 controls the scan section 2 in such a manner that the scan section 2 executes scans for the subject 40. The operation console section 3 generates an image of the subject 40, based on magnetic resonance signals obtained by the scans executed by the scan section 2 and displays the generated image.

Respective parts that constitute the operation console section 3 will be described sequentially.

The RF driver 22 has a gate modulator (not shown), an RF power amplifier (not shown) and an RF oscillator (not shown) to form a high frequency magnetic field within the static magnetic field space 11 by driving the RF coil unit 14. The RF driver 22 modulates an RF signal sent from the RF oscillator to a signal having predetermined timing and predetermined envelope using the gate modulator on the basis of the control signal outputted from the controller 25. The RF signal modulated by the gate modulator is amplified by the RF power amplifier, followed by being outputted to the RF coil unit 14.

The gradient driver 23 drives the gradient coil unit 13 based on the control signal of the controller 25 to generate a gradient magnetic field within the static magnetic field space 11. The gradient driver 23 has three-system drive circuits (not shown) in association with the three-system gradient coils of the gradient coil unit 13.

The data acquisition unit 24 has a phase detector (not shown) and an analog/digital converter (not shown) to collect or acquire the magnetic resonance signals received by the RF coil unit 14. The data acquisition unit 24 phase-detects each magnetic resonance signal sent from the RF coil unit 14 by the phase detector with the output of the RF oscillator of the RF driver 22 as a reference signal, and outputs the phase-detected signal to the analog/digital converter. Then, the data acquisition unit 24 converts the magnetic resonance signal corresponding to the analog signal phase-detected by the phase detector into a digital signal by means of the analog/digital converter and outputs it therefrom.

In the present embodiment, the data acquisition unit 24 outputs a magnetic resonance signal obtained as imaging data by the imaging sequence executed by the scan section 2 and a magnetic resonance signal obtained as navigator data by the navigator sequence to the storage unit 26 and navigator data processor 32 to be described later.

The controller 25 has a computer and a memory that records a program that allows each part to execute an operation corresponding to a predetermined scan using the computer. The controller 25 is connected to the operation unit 35 to be described later. The controller 25 processes an operation signal inputted to the operation unit 35 and outputs a control signal to the respective parts of the cradle 15, RF driver 22, gradient driver 23 and data acquisition unit 24 to control them. In order to acquire a desired image, the controller 25 controls the navigator data processor, RF pulse determinater 31, display unit 36 and the like, based on the operation signal sent from the operation unit 35.

In the present embodiment, the controller 25 controls the RF driver 22 and the gradient driver 23 to allow the scan section 2 to execute the navigator sequence NS and the imaging sequence IS.

The storage unit 26 has a computer and a memory that records a program for causing the computer to execute predetermined data processing. The storage unit 26 stores therein navigator data prior to data processing acquired by the data acquisition unit 24, imaging data corresponding to each magnetic resonance signal prior to image generation processing, navigator data data-processed by the navigator data processor 32 to be described later, and image data or the like subjected to the image generation processing.

The distance calculator 30 has a computer and a memory that records a program that causes the computer to execute predetermined data processing. The distance calculator 30 calculates the distance between two points selected at a tomographic image. The distance calculator 30 outputs the calculated distance between the two points to the RF pulse determinater 31 connected thereto.

In the present embodiment, the distance calculator 30 calculates the distance between the two points desired to be excited on the axial transverse section image stored in the storage unit 26 such as shown in FIG. 2 and outputs the same to the RF pulse determinater 31.

The RF pulse determinater 31 has a computer and a memory that records a program that causes the computer to execute predetermined processing. The RF pulse determinater 31 decides an RF pulse to be sent from the RF coil unit 14 to the subject 40, based on the distance between the two points A and B, which has been calculated by the distance calculator 30.

In the present embodiment, the navigator pulse is of an RF pulse for exciting a region body-moved in the navigator area and a region different from the region body-moved therein simultaneously. As shown in FIG. 2, for example, the region body-moved in the navigator area is of the liver 61 or lung 60, and the region different from the body-moved region is of the subcutaneous fat 63. This subcutaneous fat 63 corresponds to, for example, a subcutaneous fat 63 lying on the plane or surface that orthogonally intersects with the navigator area.

As a pulse for exciting only a cylindrical area as a navigator area, may be mentioned, a pencil beam.

As shown in FIG. 3, the pencil beam generates a gradient magnetic field in such a manner that it takes or assumes a spiral trajectory outside as viewed from the center of the k space or in the center thereof as viewed from outside. The number of turns of a spiral trajectory in the k space is determined by the RF pulse determinater 31, based on the distance between each of a plurality of regions containing a region body-moved in the navigator area to be excited and a region different from the plural regions, e.g., the distance between the liver 61 and the subcutaneous fat 63 to decide the distance between the main lobe and each side lobe in the post-excitation transverse magnetization.

As a method for determining the number of turns of the spiral trajectory in the k space, the RF pulse determinater 31 is provided with the memory having data about the distance between the regions desired to be excited and the number of turns, and determines the number of turns, based on the data.

The navigator pulse may be such an RF pulse as to excite a plurality of different regions simultaneously. The navigator pulse is not limited to the pencil beam. Even in this case, the RF pulse determinater 31 decides such an RF pulse as to excite only the plurality of different regions.

The navigator data processor 32 has a computer and a memory that records a program that causes the computer to execute predetermined data processing. The navigator data processor 32 performs data processing on navigator data corresponding to each magnetic resonance signal obtained by executing the navigator sequence by means of the scan section 2 to generate displacement information about each body-moved region.

In the present embodiment, as the body-moved region, may be mentioned, for example, a diaphragm. The navigator data processor 32 generates displacement information about the diaphragm from the navigator data. The navigator data processor 32 generate, for example, a position profile indicative of the relationship between the position of the diaphragm and time in the navigator area as the diaphragm displacement information and outputs the same to the raw data selector 33 to be described later.

The raw data selector 33 has a computer and a memory that records a program that causes the computer to execute predetermined data processing. The raw data selector 33 performs data processing for selecting as raw data, imaging data obtained by carrying out the imaging sequence by means of the scan section 2, based on the displacement information about the body-moved region generated by the navigator data processor 32.

In the present embodiment, for example, the raw data selector 33 determines whether the position profile of the diaphragm generated by the navigator data processor 32 falls within an allowable range AW set in advance. The raw data selector 33 selects imaging data corresponding to the navigator data by which the position profile lying within the allowable range AW has been generated. When upon an actual scan, for example, the navigator sequence NS is first performed and the imaging sequence IF is then carried out to acquire navigator data and imaging data, the raw data selector 33 selects the imaging data obtained by the imaging sequence performed subsequently to the navigator sequence as raw data.

The image generator 34 has a computer and a memory that records a program that allows the computer to execute predetermined data processing. The image generator 34 reconstructs a slice image about each slice of the subject 40 from the imaging data selected as the raw data by the raw data selector 33, based on a control signal outputted from the controller 25. The image generator 34 outputs the generated image to the display unit 36.

The operation unit 35 is made up of operation devices such as a keyboard, a mouse and the like. The operation unit 35 inputs operation data, an imaging protocol and the like therein through an operator. Further, the operation unit 35 sets an area for executing the imaging sequence IS and an area for executing the navigator sequence NS and outputs the operation data, the imaging protocol and data related to each setting area to the controller 25.

The display unit 36 is constituted of a display device such as a display and displays an image on its display screen, based on a control signal outputted from the controller 25. The display unit 36 displays, for example, an image about each input term for operation data inputted to the operation unit 35 by the operator on the display screen. The display unit 36 displays the slice image of the subject 40 generated by the image generator 34.

Operation

The operation of imaging or photographing the subject 40 will be explained below using the magnetic resonance imaging apparatus 1 according to the present embodiment.

Figure 5:
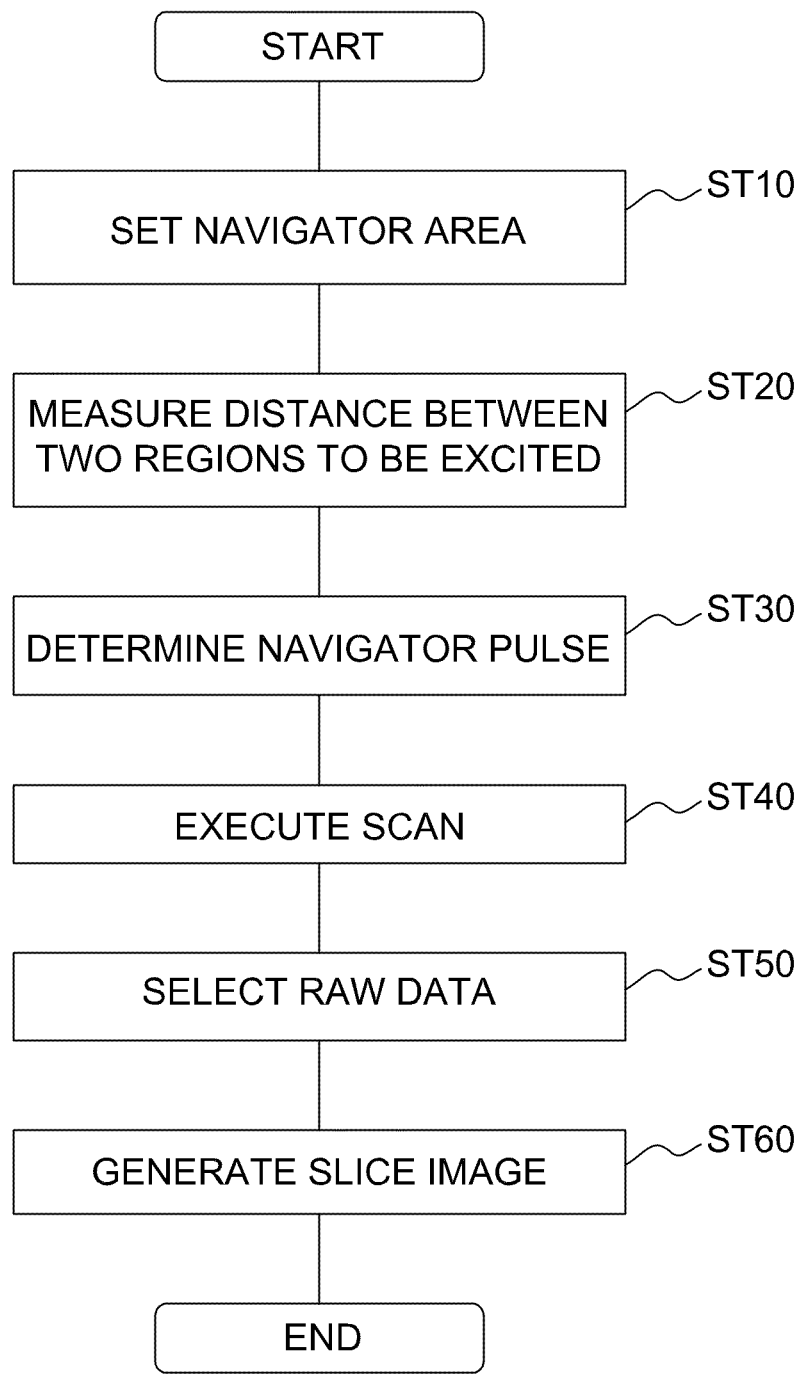
FIG. 5 is a flow chart showing the operation of imaging the subject using the magnetic resonance imaging apparatus shown in FIG. 1.

FIG. 5 is a flow chart showing the operation of imaging the subject in the one embodiment according to the invention.

As shown in FIG. 5, a navigator area is first set (ST10).

Figures 6, 7:
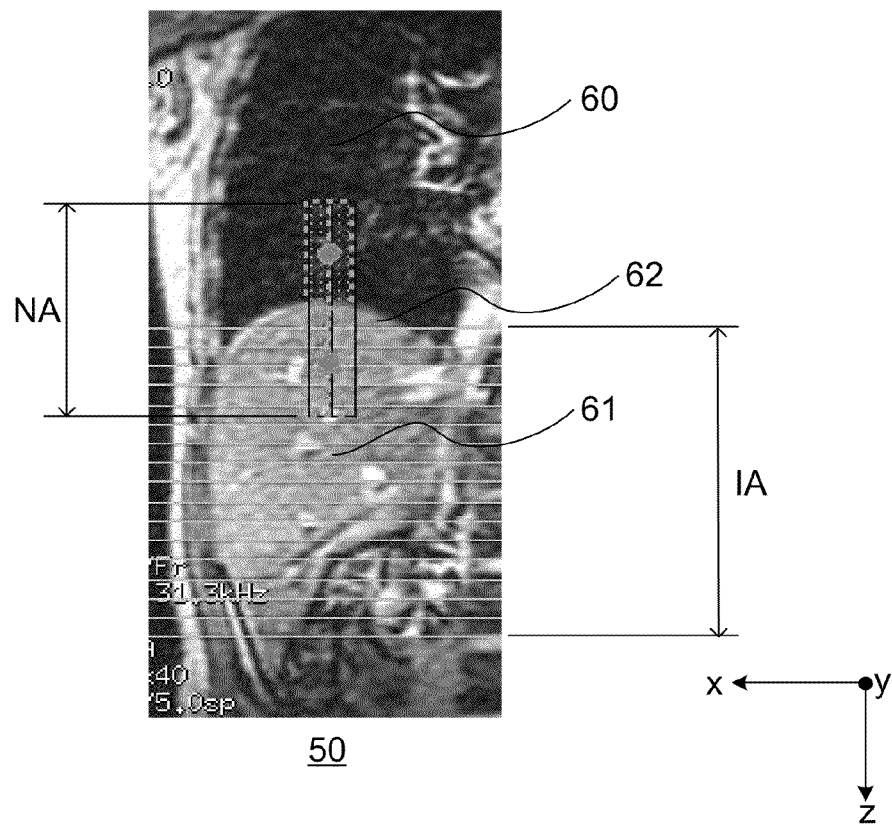
FIG. 6 is a diagram depicting a coronal image indicating a navigator area NA and an imaging area IA that may be used during the operation shown in FIG. 5.
FIG. 7 is a diagram showing the relationship between the distance between a main lobe and each side lobe, and the number of turns of a spiral trajectory of navigator data in a k space during the operation shown in FIG. 5.

FIG. 6 is a diagram showing a coronal image indicative of a navigate area NA and an imaging area IA in the one embodiment according to the invention. A z direction in FIG. 6 corresponds to the direction of the position of a vertical axis in FIG. 10 to be described later. Incidentally, here, a black area indicates the lung. A gray area indicates the liver, and the diaphragm is located between the lung and the liver. A rectangular area having long sides each disposed in the direction of a z axis approximately orthogonal to the diaphragm corresponds to the navigator area NA in which a navigator sequence NS is executed. At the liver in the coronal image, an area disposed so as to become parallel to the direction of an x axis approximately parallel to the diaphragm corresponds to the imaging area IA in which the imaging sequence IS is carried out.

Here, the navigator area NA for executing the navigator sequence NS is set onto the coronal image shown in FIG. 6.

Described specifically, the display unit 36 displays a coronal image 50 as shown in FIG. 6. For instance, an operator sets an area for carrying out a navigator sequence onto the coronal image 50 displayed by the display unit 36 through the operation unit 35 as the navigator area NA. At this time, the navigator area NA is set so as to contain a body-moved region and contain two regions whose signal intensities obtained from navigator data differ. The set navigator area NA may overlap with the imaging area IA in which the imaging sequence IS is carried out. In the present embodiment as shown in FIG. 6, the navigator area NA is set as, for example, a rectangular area having long sides each parallel to the z-axis direction which intersects with the diaphragm 62 located between the lung 60 and the liver 61 and is approximately orthogonal to the diaphragm 62. Incidentally, any one of an axial section, a coronal section and a sagittal section may be used as the section of the subject 40.

Next, as shown in FIG. 5, the distance between the two regions to be excited is calculated (ST20).

Here, the distance between the navigator area NA excited by an RF pulse to obtain a magnetic resonance signal, and a region different from the navigator area NA is measured on the axial transverse section of the subject 40. Here, the phase of navigator data of the region different from the navigator area NA is different from the phase of at least one region of the navigator data obtained from the navigator area.

Described specifically, the distance between a point A on the liver 61 lying on the axial transverse section and a point B on the subcutaneous fat 63 lying thereon as shown in FIG. 2, for example is measured. In this case, the positions desired to be excited on the axial transverse section shown in the display unit 36 are selected and thereby the distance calculator 30 calculates the distance between the two points.

Next, as shown in FIG. 5, a navigator pulse is determined (ST30).

Here, the RF pulse determinater 31 determines a navigator RF pulse and a gradient magnetic field, based on the distance between the two regions to be excited, which has been calculated at Step ST20.

In the present embodiment, the navigator pulse is of an RF pulse for exciting the navigator area NA and the region different from the navigator area NA simultaneously. The RF pulse excites the navigator area NA and the region different from the navigator area NA in such a manner that the intensity of a navigator data signal obtained from the region different from the navigator area NA falls between the intensities of navigator data signals obtained from the navigator area NA.

For example, as the navigator pulse for exciting the different regions simultaneously, may be mentioned, for example, a pencil beam.

Here, FIG. 7 is a diagram showing the relationship between the distance between a main lobe and its corresponding side lobe, and the number of turns of a spiral trajectory at the excitation of the pencil beam in the one embodiment according to the invention.

In one example in which excitation is conducted using an RF pulse having a length of 4 ms at a device having a maximum gradient magnetic field strength of 33 [mT/m] and a maximum Slew Rate of 120 [T/m/s], the distance between the main lobe and its corresponding side lobe is about 25 cm where the number of turns of the spiral trajectory at the excitation of the pencil beam is eight. When the number of turns of the spiral trajectory at the pencil beam excitation is six, the distance between the main lobe and its corresponding side lobe is about 18.8 cm. As the number of turns of a spiral trajectory of navigator data in a k space decreases, the distance between the main lobe and the side lobe becomes shorter. Thus, when the number of turns of the spiral trajectory of the navigator data in the k space changes, the distance between the central main lobe and its corresponding side lobe changes.

The number of turns is adjusted using this principle to excite each region desired to be excited.

In the present embodiment, for example, the region body-moved in the navigator area is of a diaphragm 62, and the plural regions containing the body-moved region are of a liver 61 and a lung 60. The region different from the plural regions containing the body-moved region is of a subcutaneous fat 63. This subcutaneous fat 63 is of, for example, a subcutaneous fat 63 lying on the plane or surface that vertically intersects with the navigator area.

As to the transverse magnetization formed immediately after the excitation by the pencil beam as shown in FIG. 4, the main lobe large in transverse magnetization is disposed in the center, and the side lobes smaller in transverse magnetization than the main lobe are disposed on both sides. In the present embodiment, the navigator pulse is determined in such a manner that the main lobe is located in the liver 61 and the lung 60, and each side lobe is located in the subcutaneous fat 63.

Described specifically, as shown in FIG. 7, data about the relationship between the distance between the main lobe and each side lobe and the number of turns of the spiral trajectory at the excitation of the pencil beam is calculated in advance. This data is stored in the memory of the RF pulse determinater 31, and the number of turns corresponding to the distance between the two regions to be excited, which has been calculated by the distance calculator 30 at Step ST20, is determined. Consequently, a navigator pulse is decided.

Next, a scan is executed as shown in FIG. 5 (ST40).

Here, the scan section 2 executes the navigator sequence NS for transmitting the navigator pulse decided at Step ST30 on the navigator area NA of the subject 40, which has been set at Step ST10 and executes the imaging sequence IS at the imaging area IA alternately with respect to the navigator sequence NS.

Figure 8:
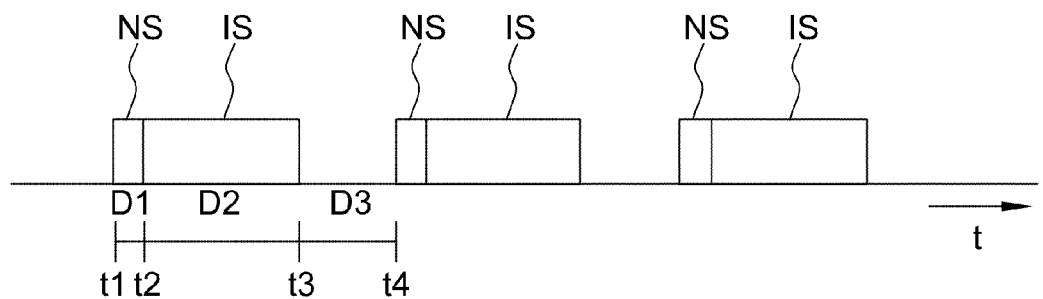
FIG. 8 is a sequence diagram illustrating a sequence used when a subject is scanned during the operation shown in FIG. 5.
Figure 9:
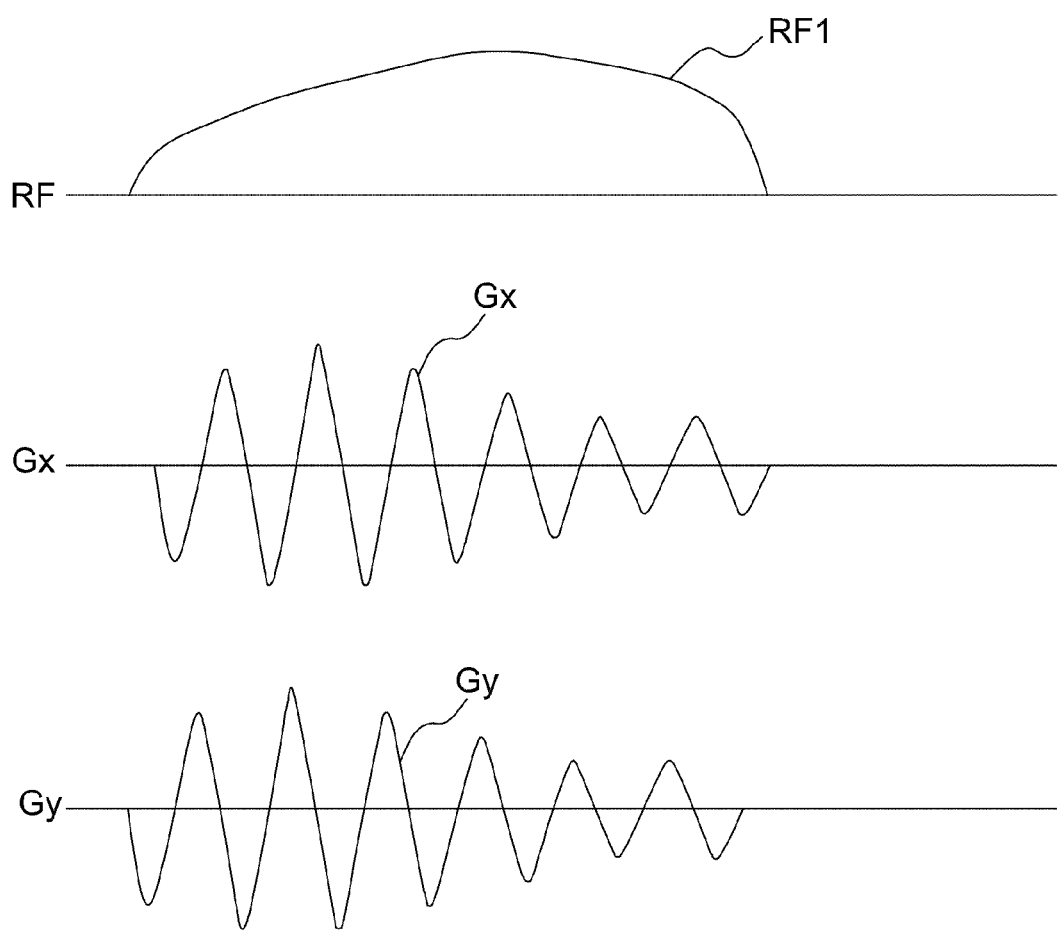
FIG. 9 is a diagram showing excitation pulses in a navigator sequence executed during the operation shown in FIG. 5.

FIG. 8 is a sequence diagram showing a sequence used when the subject 40 is scanned in the one embodiment according to the invention. The horizontal axis indicates a time base t. FIG. 9 is a diagram showing an excitation pulse where the navigator sequence using the pencil beam in the one embodiment according to the invention is executed. Gx indicates an x-direction gradient magnetic field, Gy indicates a y-direction gradient magnetic field and RF indicates a high frequency pulse, respectively. Incidentally, the vertical axis indicates the intensity and the horizontal axis indicates time here.

Described specifically, for example, the scan section 2 executes a navigator sequence NS between a time t1 at which the navigator sequence NS is started, and a time t2 at which a predetermined time D1 has elapsed, as an actual scan as shown in FIG. 8. Then, the scan section 2 executes an imaging sequence IS between the time t2 and a time t3 at which a predetermined time D2 has elapsed. The scan section 2 executes a navigator sequence NS between the time t3 and a time t4 at which a predetermined time D3 has elapsed.

The imaging sequence IS is first performed and thereafter the navigator sequence NS may be conducted.

When the RF pulse RF1 is transmitted at the navigator area NA under the navigator sequence NS as shown in FIG. 9, the x-direction gradient magnetic field Gx and the y-direction gradient magnetic field Gy are applied in such a manner that their polarities change continuously one after another.

As shown in FIG. 4, a magnetic resonance signal set as the main lobe is obtained as navigator echo data. A magnetic resonance signal excited by each side lobe from the region different from the region contained in the navigator area NA is also contained in the navigator echo data obtained here. The data acquisition unit 24 collects or acquires the magnetic resonance signals obtained as the navigator echo data by the execution of the navigator sequence NS and outputs the same to the navigator data processor 32.

Next, the selection of raw data is conducted as shown in FIG. 5 (ST50).

Here, the navigator data processor 32 performs data processing on the navigator data acquired by executing the navigator sequence NS at Step ST40. The raw data selector 33 selects imaging data as raw data, based on the processed data.

In the present embodiment, the raw data selector 33 selects imaging data as raw data, based on the displacement of the diaphragm 62 of the subject 40 due to the motion of breathing.

Figure 10:
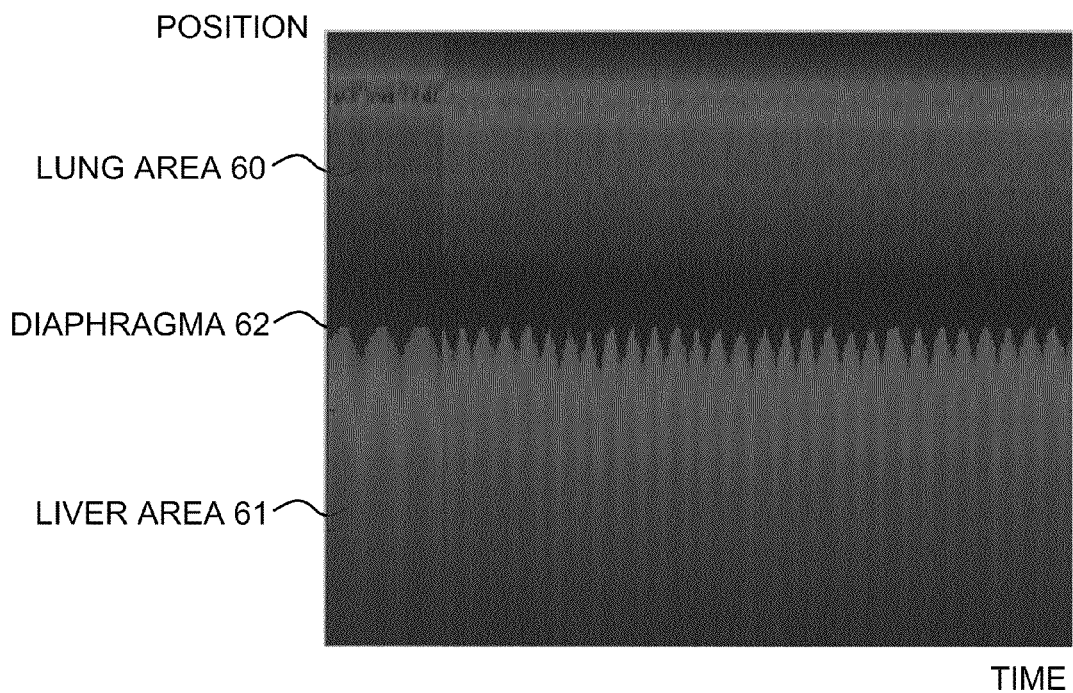
FIG. 10 is a diagram showing a position profile indicative of the relationship between the position of a diaphragm and time during the operation shown in FIG. 5.

FIG. 10 is a diagram showing a position profile indicative of the relationship between the position of a diaphragm and time in the one embodiment according to the invention.

Described specifically, a position profile indicative of the relationship between the phase of navigator data obtained by executing the navigator sequence NS by means of the scan section 2 and the position in the navigate area is generated. Thereafter, the position of a diaphragm 62 is detected at the position profile. As shown in FIG. 10, a position profile indicative of the relationship between the position of the diaphragm 62 corresponding to the boundary between a lung 60 and a liver 61 and the time at which the navigator data is acquired, is generated. Then, the raw data selector 33 acquires imaging data as raw data, based on the generated position profile.

The position profile employed in the present embodiment is capable of accurately detecting the diaphragm 62 corresponding to a region at the boundary between the lung 60 and the liver 61 as shown in FIG. 10.

As a method for determining whether the imaging data is acquired as the raw data, based on the position profile, the following is mentioned. For example, the raw data selector 33 determines whether the position at the position profile falls within an allowable range AW set in advance. When the position falls within the allowable range AW, the raw data selector 33 selects as raw data, imaging data acquired by the imaging sequence IS subsequent to the execution of the navigator sequence NS by which the navigator data in the allowable range AW has been acquired.

Next, a slice image is generated as shown in FIG. 5 (ST60). Here, the image generator 34 generates a slice image about a slice surface of the subject 40, based on the raw data selected by the raw data selector 33 at Step ST50. The image generator 34 outputs the generated slice image to the display unit 36.

In the one embodiment of the invention as described above, the distance calculator 30 measures, on the axial transverse section, the distance between the different regions each desired to obtain the magnetic resonance signal by execution of its excitation by the RF pulse. The RF pulse determinater 31 determines the navigator pulse, based on the distance. Then the scan section 2 executes the navigator sequence NS for transmitting the navigator pulse decided by the RF pulse determinater 31, in the navigator area NA of the subject 40 and executes the imaging sequence IS in the imaging area IA with respect to the navigator sequence NS alternately. The navigator data processor 32 executes data processing on the plural navigator data acquired by executing the navigator sequence NS. The raw data selector 33 selects the corresponding imaging data as the raw data, based on the processed data. The corresponding slice image is generated based on the raw data.

Thus, when the boundary (diaphragm 62, for example) between a region (lung 60, for example) almost occupied by air and low in spin density, which is excited and a region (liver 61, for example) high in spin density, which is excited, is detected, a region (subcutaneous fat 63, for example) different from the originally-excited region is excited simultaneously. The intensity of a navigator data signal obtained from the region different therefrom is set between the intensities of respective navigator data signals at the region low in spin density and the region high in spin density, whereby a phase signal from the different region appears in the intensity of the navigator data signal at the region low in spin density, and the region high in spin density is not so affected by the phase signal from the different region.

Figure 15:
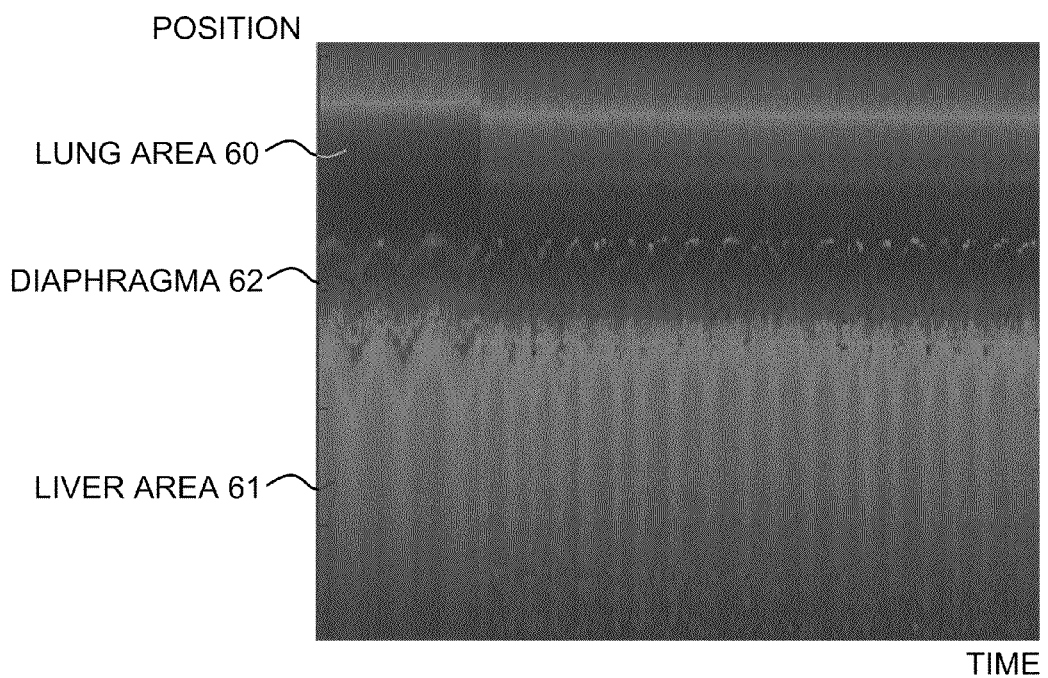
FIG. 15 is a diagram illustrating a position profile indicative of the relationship between the position of a diaphragm and time, for describing the related art.

Since the intensity of the signal in a liver area is conventionally low as shown in FIG. 15, the signal intensity is susceptible to change due to noise. Further, the position of the diaphragm 62 lying in the boundary between the lung 60 and the liver 61 could not be detected accurately. Since, however, the intensity of the signal appears in the lung area in the one embodiment of the invention, the change in the signal intensity due to the noise is hard to occur, and the diaphragm 62 corresponding to the boundary between the lung 60 and the liver 61 can be detected accurately. It is thus possible to obtain respiratory information accurately and obtain a slice image low in artifacts.

Since the position of the diaphragm 62 can be detected accurately, a detection error can be reduced and the shortening of an imaging time interval can be achieved.

Incidentally, the invention is not limited to the above embodiment upon its implementation. Various modified forms can be adopted.

Although the pencil beam has been used as the navigator pulse in the embodiment of the invention, it is not limited to this pulse, but may be of an RF pulse capable of exciting two different regions. Although the distance between different tissues to be excited is measured and the each navigator pulse is determined based on the result of measurement in the embodiment of the invention, this process may be omitted using a pulse small in the number of turns in advance where an analysis is conducted using phase information.

Figure 11:
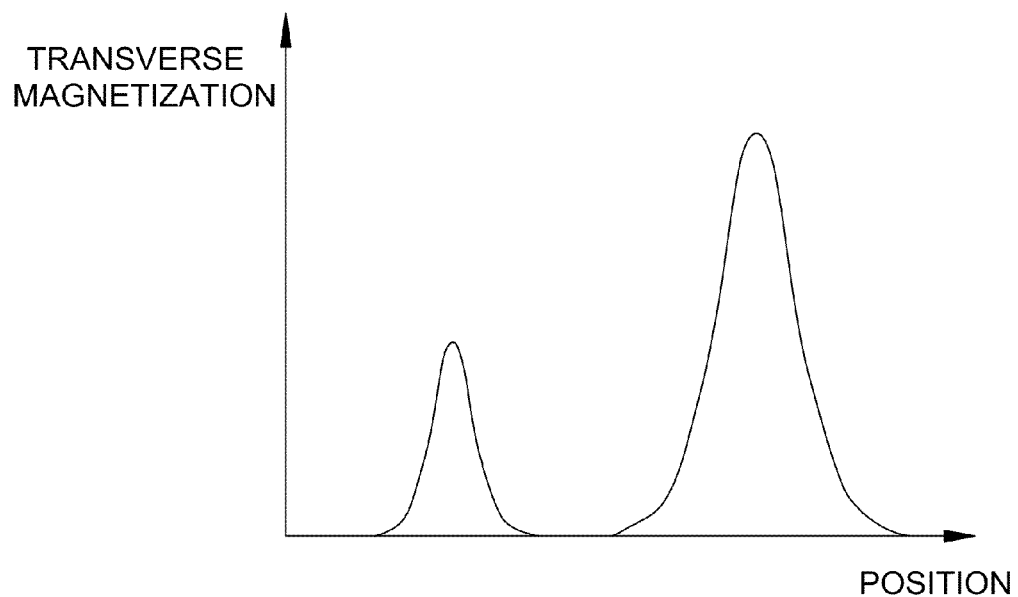
FIG. 11 is a diagram illustrating transverse magnetization formed immediately after excitation of another RF pulse during the operation shown in FIG. 5.
Figure 12:
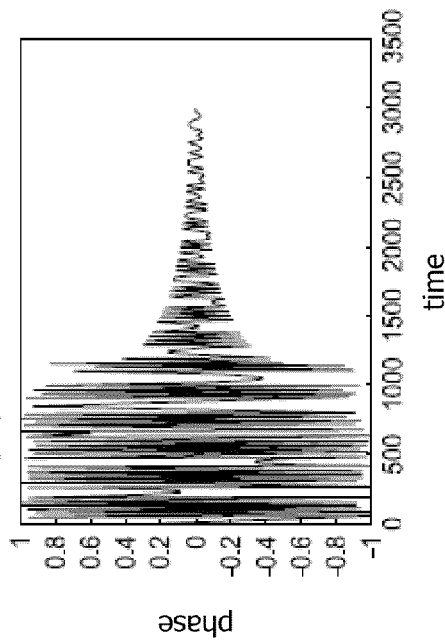
FIGS. 12(a)-12(d) show an RF pulse and gradient magnetic fields for enabling the excitation shown in FIG. 11.
Figure 12:
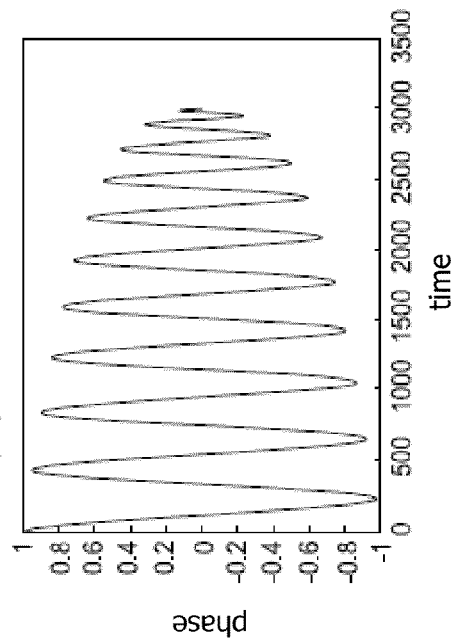
Figure 12:
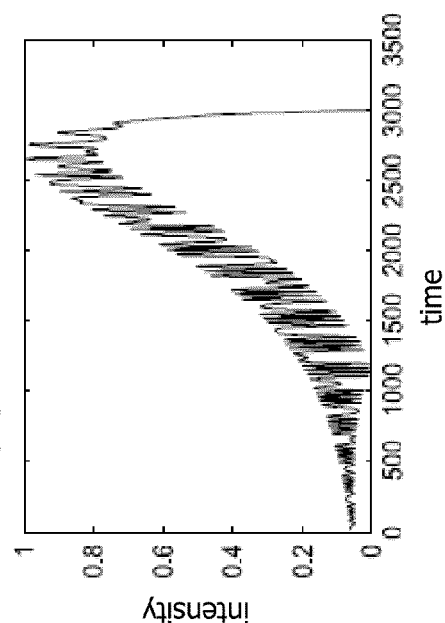
Figure 12:
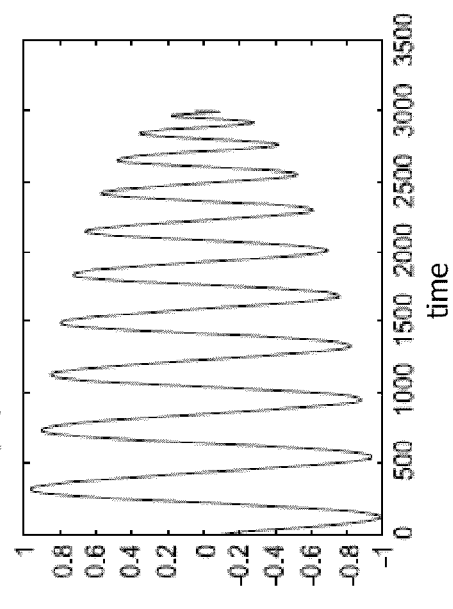
Figure 13:
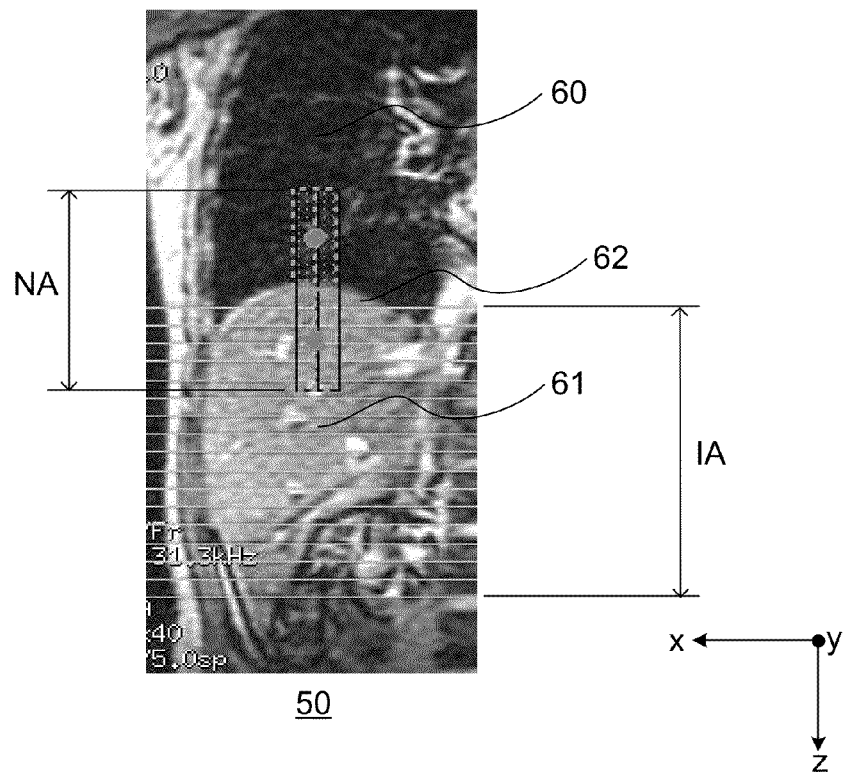
FIG. 13 is a diagram showing a coronal image indicative of a navigator area N and an imaging area IA for describing a related art.
Figure 14:
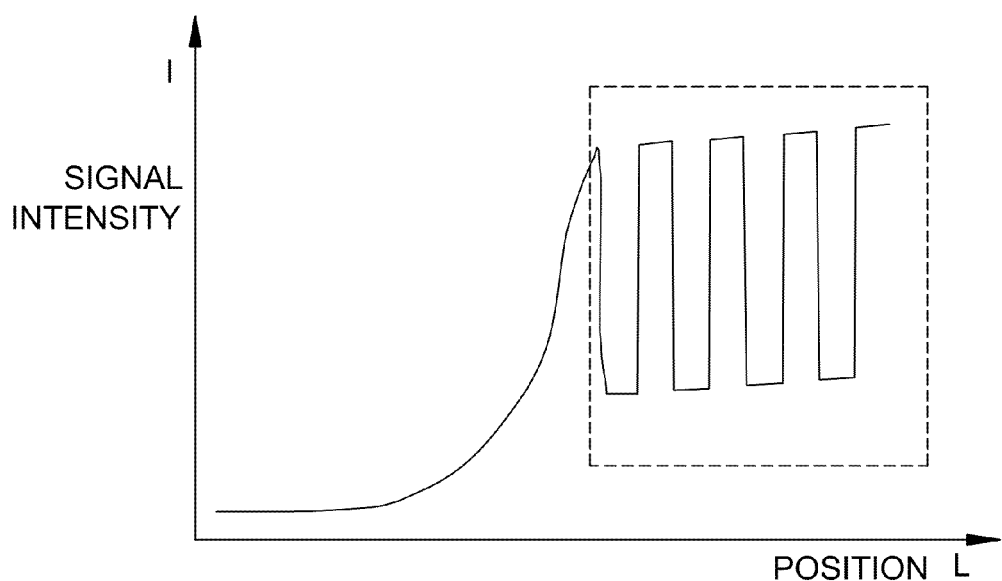
FIG. 14 is a diagram showing a signal intensity profile for describing the related art.

FIG. 11 is a diagram showing transverse magnetization formed immediately after excitation of another RF pulse in the one embodiment according to the invention. FIGS. 12(*a*)-12(*d*) show an RF pulse and gradient magnetic fields for enabling the excitation shown in FIG. 11. FIG. 12(*a*) shows the intensity of the RF pulse, FIG. 12(*b*) shows the phase of the RF pulse, FIG. 12(c) shows an x-direction gradient magnetic field, and FIG. 12(d) shows a y-direction gradient magnetic field, respectively.

As shown in FIG. 11, large transverse magnetization is generated in the liver 61 and small transverse magnetization is generated in the subcutaneous fat 63. In order to realize such transverse magnetization, the RF pulse shown in each of FIGS. 12(a) and 12(b) is applied in the gradient magnetic fields shown in FIGS. 12(c) and 12(d). The RF pulse to be applied can be designed by any suitable method known within the art. At this time, the timings provided to apply the RF pulse shown in each of FIGS. 12(a) and 12(b) and the gradient magnetic field shown in each of FIGS. 12(c) and 12(d) are the same as when the pencil beam shown in FIG. 9 is used.

An advantage similar to the pencil beam is brought about by applying such an RF pulse to an area containing a body-moved region. Thus, even in this case, respiratory information can be obtained accurately, and a slice image low in artifacts can be obtained.

Since the position of the diaphragm 62 can be detected accurately, a detection error is reduced and the shortening of an imaging time interval is achieved.

Many widely different embodiments of the invention may be configured without departing from the spirit and the scope of the present invention. It should be understood that the present invention is not limited to the specific embodiments described in the specification, except as defined in the appended claims.

What is claimed is:

1. A magnetic resonance imaging apparatus comprising:
a scan section having an RF coil unit configured to execute a navigator sequence which transmits an RF pulse to a subject to obtain each magnetic resonance signal as navigator data and configured to execute an imaging sequence for imaging an abdominal region and to correct an excitation section according to a detected position of a diaphragm using the navigator data;
wherein upon execution of the navigator sequence, the RF coil unit is configured to simultaneously excite a first region inside a navigator area, a second region inside the navigator area, and a third region located outside of the navigator area in a plane orthogonal to the navigator area at the same time, wherein the first region is a lung, the second region is a liver, and the third region is a subcutaneous fat, wherein the first and second regions include at least a body-moved region positioned therebetween, the body-moved region including a diaphragm; and
a navigator data processor configured to generate a position profile indicative of the relationship between positions of the diaphragm and time based on a phase of the navigator data.

2. The magnetic resonance imaging apparatus according to claim 1, wherein the RF coil unit is configured to transmit the RF pulse such that an intensity of a navigator data signal obtained from the third region falls between the intensities of the navigator data signals obtained from the first and second regions.

3. The magnetic resonance imaging apparatus according to claim 1, wherein the RF coil unit is configured to execute the navigator sequence such that the phase of navigator data obtained from the subcutaneous fat differs from the phase of navigator data obtained from the liver.

4. The magnetic resonance imaging apparatus according to claim 3, wherein the RF coil unit is configured to execute the navigator sequence such that the intensity of a navigator data signal obtained from the subcutaneous fat is lower than the intensity of a navigator data signal obtained from the liver.

5. The magnetic resonance imaging apparatus according to claim 1, wherein the RF coil unit is configured to execute the navigator sequence such that, upon excitation of the navigator sequence, a gradient magnetic field assumes a spiral trajectory on a k space.

6. The magnetic resonance imaging apparatus according to claim 1, wherein the RF coil unit is configured to transmit RF pulses for exciting the first and second regions and the third region in cylindrical form respectively.

7. The magnetic resonance imaging apparatus according to claim 5, wherein a number of turns at the time that the gradient magnetic field assumes a spiral trajectory on a k space, is determined based on a distance interval between the navigator area and the third region.

8. The magnetic resonance imaging apparatus according to claim 5, wherein the gradient magnetic field is generated so as to assume a spiral trajectory outside as viewed from the center of the k space.

9. The magnetic resonance imaging apparatus according to claim 5, wherein the gradient magnetic field is generated so as to assume a spiral trajectory in the center of the k space as viewed from outside the k space.

10. An RF pulse applying method comprising:
executing, by a processor, a navigator sequence for transmitting an RF pulse to a subject and thereby obtaining each magnetic resonance signal as navigator data;
generating a position profile indicative of the relationship between positions of the diaphragm and time based on a phase of the navigator data; and
executing an imaging sequence for imaging an abdominal region and to correct and excitation section according to a detected position of a diaphragm using the navigator data;
wherein executing the navigator sequence comprises:
simultaneously exciting a first region inside a navigator area, a second region inside the navigator area, and a third region located outside of the navigator area in a plane orthogonal to the navigator area at the same time, wherein intensities of different navigator data signals are obtained from the first and second regions, and wherein one of the first and second regions is a body-moved region, wherein the first region is a lung, the second region is a liver, the third region is a subcutaneous fat, and the body-moved region is a diaphragm, and wherein the simultaneously exciting a first region comprises transmitting the RF pulse to the subcutaneous fat set as the third region.

11. The RF pulse applying method according to claim 10, wherein simultaneously exciting a first region comprises transmitting the RF pulse such that an intensity of a navigator data signal obtained from the third region falls between the intensities of the navigator data signals obtained from the first and second regions.

12. The RF pulse applying method according to claim 10, wherein simultaneously exciting a first region comprises executing the navigator sequence such that a phase of navigator data obtained from the subcutaneous fat differs from a phase of navigator data obtained from the liver.

13. The RF pulse applying method according to claim 12, wherein simultaneously exciting a first region comprises executing the navigator sequence such that an intensity of a navigator data signal obtained from the subcutaneous fat is lower than an intensity of a navigator data signal obtained from the liver.

14. The RF pulse applying method according to claim 10, wherein simultaneously exciting a first region comprises executing the navigator sequence such that, upon excitation of the navigator sequence, a gradient magnetic field assumes a spiral trajectory in a k space.

15. The RF pulse applying method according to claim 10, wherein simultaneously exciting a first region comprises transmitting RF pulses for exciting the first and second regions and the third region in cylindrical form respectively.

16. The RF pulse applying method according to claim 14, further comprising determining a number of turns at a time that the gradient magnetic assumes the spiral trajectory on the k space, based on a distance interval between the navigator area and the third region.

* * * * *